United States Patent
Dennerlein et al.

(10) Patent No.: US 8,619,944 B2
(45) Date of Patent: Dec. 31, 2013

(54) METHOD AND DEVICE FOR DETERMINING IMAGES FROM X-RAY PROJECTIONS

(75) Inventors: Frank Dennerlein, Forchheim (DE); Stefan Hoppe, Amberg (DE); Markus Kowarschik, Langenzenn (DE); Holger Scherl, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 847 days.

(21) Appl. No.: 12/772,793

(22) Filed: May 3, 2010

(65) Prior Publication Data

US 2010/0286928 A1    Nov. 11, 2010

(30) Foreign Application Priority Data

May 8, 2009    (DE) .................. 10 2009 020 400

(51) Int. Cl.
*A61B 6/03*    (2006.01)
(52) U.S. Cl.
USPC ........................................................ 378/15
(58) Field of Classification Search
USPC .................................. 378/4, 15, 901; 382/131
See application file for complete search history.

(56) References Cited

U.S. PATENT DOCUMENTS

| | | | | |
|---|---|---|---|---|
| 6,125,167 A * | 9/2000 | Morgan | | 378/124 |
| 6,229,870 B1 * | 5/2001 | Morgan | | 378/9 |
| 6,754,300 B2 * | 6/2004 | Hsieh et al. | | 378/16 |
| 6,771,733 B2 | 8/2004 | Katsevich | | |
| 6,990,167 B2 | 1/2006 | Chen | | |
| 6,990,170 B2 * | 1/2006 | Sugihara et al. | | 378/15 |
| 7,280,631 B2 * | 10/2007 | De Man et al. | | 378/10 |
| 7,359,477 B2 * | 4/2008 | Lauritsch et al. | | 378/4 |
| 7,403,587 B2 * | 7/2008 | Bontus et al. | | 378/4 |
| 7,616,731 B2 * | 11/2009 | Pack et al. | | 378/10 |
| 7,639,774 B2 * | 12/2009 | De Man et al. | | 378/9 |
| 7,639,775 B2 * | 12/2009 | DeMan et al. | | 378/9 |
| 7,706,499 B2 * | 4/2010 | Pack et al. | | 378/9 |
| 7,813,473 B2 * | 10/2010 | Edic et al. | | 378/8 |
| 7,826,594 B2 * | 11/2010 | Zou et al. | | 378/92 |
| 7,835,486 B2 * | 11/2010 | Basu et al. | | 378/9 |
| 7,885,375 B2 * | 2/2011 | De Man et al. | | 378/9 |
| 2005/0047542 A1 | 3/2005 | Chen | | |

OTHER PUBLICATIONS

German Office Action dated Feb. 2, 2010 for corresponding German Patent Application No. DE 10 2009 020 400.8 with English translation.
Feldkamp, L. A. et al., "Practical cone-beam algorighm," J. Opt. Soc. Am. A, vol. 1, No. 6, Jun. 1984, pp. 612-619.

(Continued)

*Primary Examiner* — Allen C. Ho
(74) *Attorney, Agent, or Firm* — Lempia Summerfield Katz LLC

(57) ABSTRACT

A method and a device for determining attenuation coefficients for an object using a movable X-ray source and a detector, which is provided for recording projections, is provided. The method includes specifying a trajectory for the movable X-ray source, specifying positions on the trajectory for determining a derivative of projections recorded by the detector, specifying a plurality of scanning positions for each of the specified positions, following the trajectory with the X-ray source and recording a projection for each scanning position, numerically calculating a projection derivative in relation to the trajectory path for each of the positions using the projections recorded for the associated plurality of scanning positions, and determining attenuation coefficients for the object from the calculated projection derivatives using a theoretically exact or approximate rule for the reconstruction.

13 Claims, 3 Drawing Sheets

(56) References Cited

OTHER PUBLICATIONS

Katsevich, Alexander, "Theoretically Exact Filtered Backprojection-Type Inversion Algorithm for Spiral CT," Siam J. Appl. Math., vol. 2, No. 6, 2002, pp. 2012-2026.

Katsevich, Alexander, "Image reconstruction for the circle and line trajectory," Phys. Med. Biol. 49, 2004, pp. 5059-5072.

Katsevich, Alexander, "Image reconstruction for the circle-and-arc trajectory," Phys. Med. Biol. 50, 2005, pp. 2249-2265.

Noo, Frederic et al., "A new scheme for view-dependant data differentiation in fan-beam and cone-beam computed tomography," Phys. Med. Biol. 52, 2007, pp. 5393-5414.

Pack, Jed D. and Frédéric Noo, "Cone-beam reconstruction using 1D filtering along the projection of $M$-lines," Inverse Problems 21, 2005, pp. 1105-1120.

Pack, Jed D. and Frédéric Noo, "Cone-Beam Reconstruction Using the Backprojection of Locally Filtered Projections," IEEE Transactions on Medical Imaging, vol. 24, No. 1, Jan. 2005, pp. 70-85.

* cited by examiner

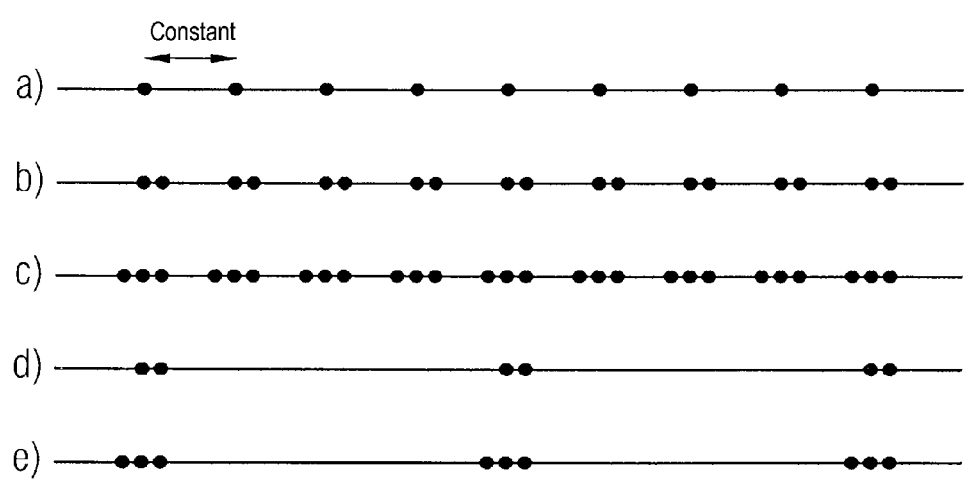

METHOD AND DEVICE FOR DETERMINING IMAGES FROM X-RAY PROJECTIONS

This application claims the benefit of DE 10 2009 020 400.8 filed May 8, 2009, which is hereby incorporated by reference.

BACKGROUND

The present embodiments relate to a method and a device for determining attenuation coefficients for an object using a movable X-ray source and a detector.

X-ray methods are standard techniques in medical engineering. With simple X-ray photographs, X-ray radiation is transmitted through an object that is to be examined and subsequently recorded by a detector. The recording or projection represents information about the attenuation of the transmitted X-ray beams on a path through the object. The attenuation of the X-ray radiation is dependent on the density of the object parts penetrated by the radiation. The density in turn yields information about the properties of the object, which are typically presented in visual form for diagnostic purposes. In the case of an X-ray photograph, the intensity registered by the detector is dependent on the overall composition of the object along the path traveled by the X-ray beam (i.e., information integrated over a distance is available). Consequently, attenuation coefficients of the object as a function of all three space coordinates are not obtained from a single X-ray photograph. For a three-dimensional image, therefore, a plurality of X-ray photographs are taken from different recording positions, and a three-dimensional image is reconstructed from the plurality of X-ray photographs. In medical engineering, this approach is adopted in computed tomography (CT). Within the framework of computed tomography, the X-ray source and X-ray detector travel along a path or trajectory, and recordings are taken along the trajectory. The recordings are used to reconstruct a three-dimensional image of attenuation coefficients, which relate to the density.

Image reconstruction is a complex, mathematical problem. Two groups of methods have become established for three-dimensional image construction: approximate and exact methods. In this context, theoretically exact methods are methods which, mathematically, include no approximations; the numerical conversion may introduce errors. The approximate methods (e.g., the Feldkamp algorithm) initially had the advantage of the significantly less complex numerical conversion. Thanks to skillful formulations of the mathematical problem, which have been proposed in the last several years, there is now available a theoretically exact formulation, which can be converted numerically with a realistic amount of effort. This is described, for example, in U.S. Pat. No. 6,771,733 B2. U.S. Pat. No. 6,771,733 B2 discloses a reconstruction formula (formula 10), which is well suited to the numerical conversion of an exact method. For implementation, this reconstruction formula generally makes use of a further transformation according to the path or trajectory used. The corresponding formula for a spiral path is expressed, for example, in the cited publication as formula 29.

In respect of the numerical conversion, however, difficulties continue to exist. One challenge that remains is finding a reasonable compromise between the number of projections recorded and the image quality, the image quality generally being higher, the more images that are recorded. However, it is also desirable to limit the number of recordings made in order to limit the exposure to radiation of patients being examined.

SUMMARY AND DESCRIPTION

The present embodiments may obviate one or more of the drawbacks or limitations in the related art. For example, in one embodiment, the number of projections in approximate and exact reconstruction methods may be reduced without a deterioration in image quality.

In the present embodiments, attenuation coefficients for an object are determined using a movable X-ray source and a detector. In this context, the term detector is to be understood in a broad sense (e.g., the detector may be a detector system having a suitable arrangement of detectors or detector surfaces). Either both the X-ray source and the detector may be movable (e.g., CT applications) or only the X-ray source may be movable (e.g., tomosynthesis in mammography). In one embodiment, the attenuation coefficients are determined using projections (e.g., recordings of X-ray radiation transmitted through the object), a path or trajectory being specified for the movable X-ray source. Positions are specified on the trajectory (e.g., equidistantly) for the numeric calculation of a derivative of projections recorded by the detector. A plurality of scanning positions (e.g., 2 or 3) is specified for each of the specified positions. The movable X-ray source travels along the trajectory, a projection being recorded for each of the specified scanning positions. In one embodiment, the trajectory may be followed at a constant speed. At a constant speed, the system used for the recordings is subject to comparatively low mechanical stresses. A constant speed may be used for the duration of the treatment, because the trajectory can be completed more quickly due to the lower mechanical loads. Accordingly, different time intervals occur between recordings of projections (e.g., shorter time intervals in the case of adjacent recordings that are assigned to the same plurality of specified scanning positions than if the adjacent recordings do not belong to the same plurality of scanning positions). The projections obtained are used for the numeric calculation of the projection derivative in relation to the trajectory, the projections recorded for the associated plurality of scanning positions being used for each of the positions. The calculated projection derivatives are used for the reconstruction using a theoretically exact or approximate rule or formula for determining the attenuation coefficients for the object. In one embodiment, further acts may be provided (e.g., for preprocessing the projections prior to the reconstruction using exact or approximate formulas). Examples of such further acts would be, for example, resorting (e.g., binning) and filtering. The acts in the numeric derivative calculation and reconstruction may also be linked to one another in such a way that a complete calculation of all derivatives is not performed before the start of the back-projection. These are measures known to the person of skill in the art, for which the person of skill in the art will make provision as a matter of routine as an embodiment of the teaching according to the present embodiments. In one embodiment, a usable theoretically exact formula or mathematical rule can be obtained, for example, by a transformation of formula 10 from U.S. Pat. No. 6,771,733 B2 for a specific trajectory (e.g., spiral, circle, or line). However, the present embodiments may also be used with approximate methods. For example, tomosynthesis is usually not exact by construction (due to the incomplete scanning path), but reconstruction methods that make use of a derivative along the trajectory are used.

Both in the case of some approximate methods and in the case of the known theoretically exact formulas that are suitable for a numeric conversion for the reconstruction for determining attenuation coefficients in three dimensions, a derivative of projections appears according to a parameter, which parameterizes the trajectory followed by the recording source. This derivative plays an important role for the numeric conversion of the formulas for the back-projection. After positions for determining derivatives of the projections recorded by the detector are specified, and scanning positions are assigned to the specified positions, the quality of the numeric derivative may be optimized by suitable specification of the scanning positions. As a result, the same quality may be achieved with fewer recordings overall. As a consequence, images may be recorded that have the same quality yet expose the patient to a lower dose of radiation.

The present embodiments also include a device through which the methods described above are implemented. The device may use software, hardware, firmware or a combination thereof in order to realize the present embodiments.

The individual acts of the methods described above may also be realized using corresponding functional software modules.

BRIEF DESCRIPTION OF THE DRAWINGS

FIG. 4 shows a number of recording protocols.

DETAILED DESCRIPTION OF THE DRAWINGS

Figure 1:
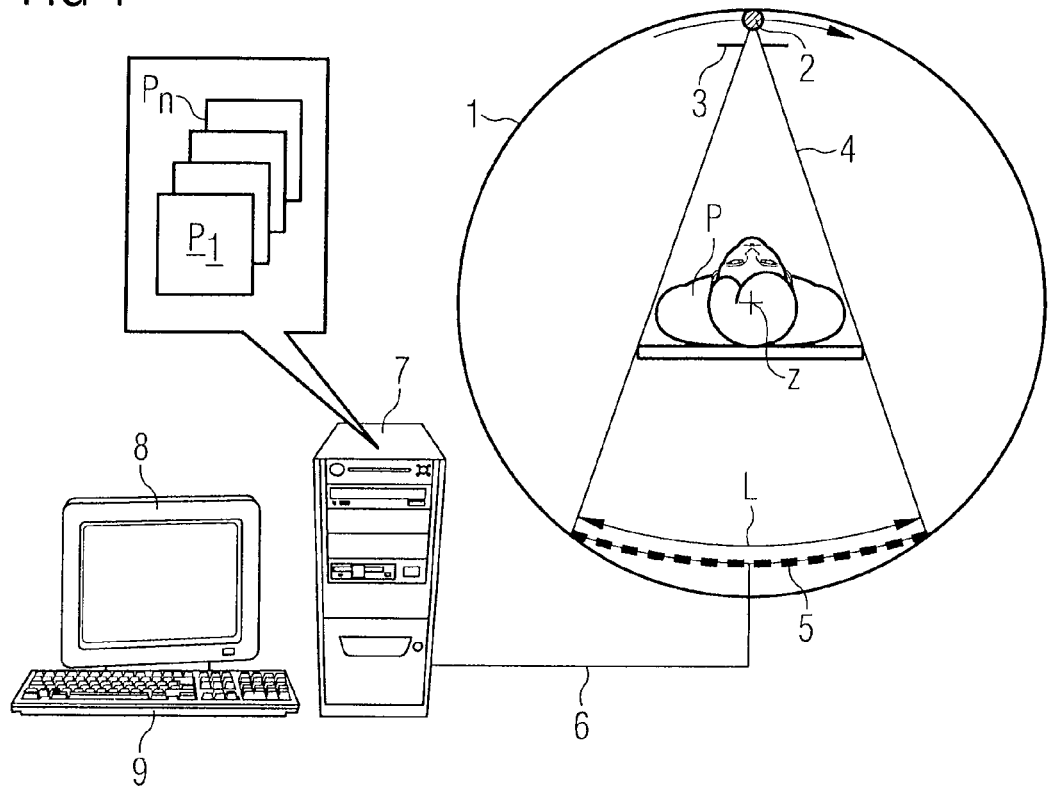
FIG. 1 shows a schematic representation of a spiral CT scanner having multiple rows of detector elements in the z-direction.
Figure 2:
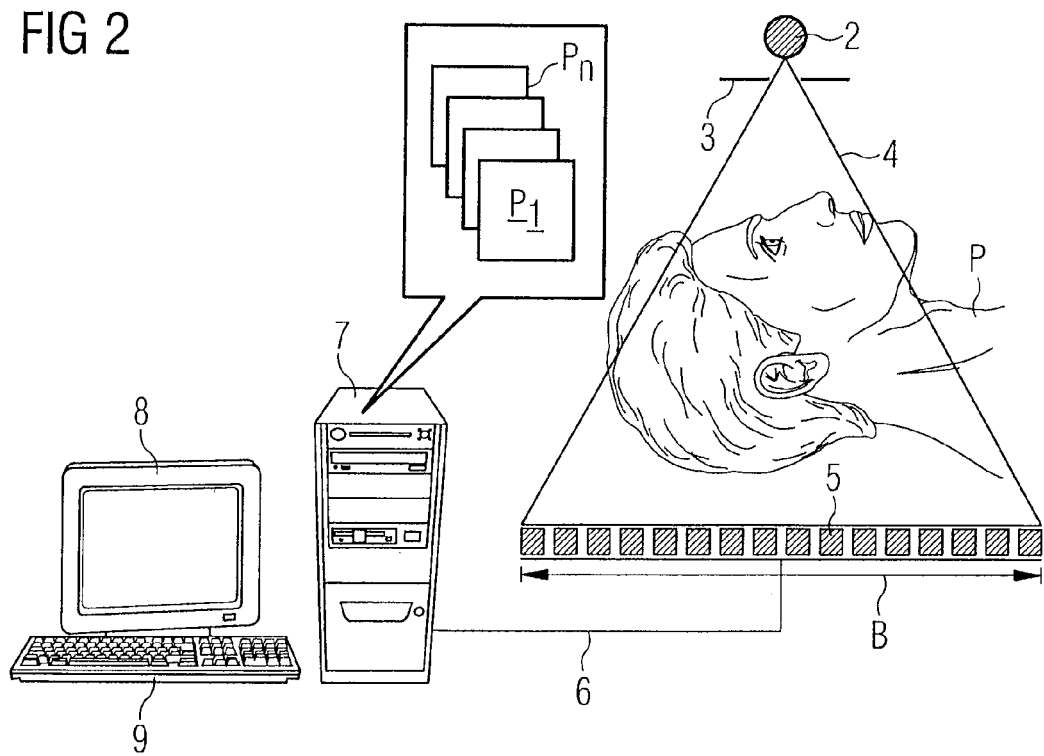
FIG. 2 shows a longitudinal section along the z-axis through the spiral CT scanner according to FIG. 1.
Figure 3:
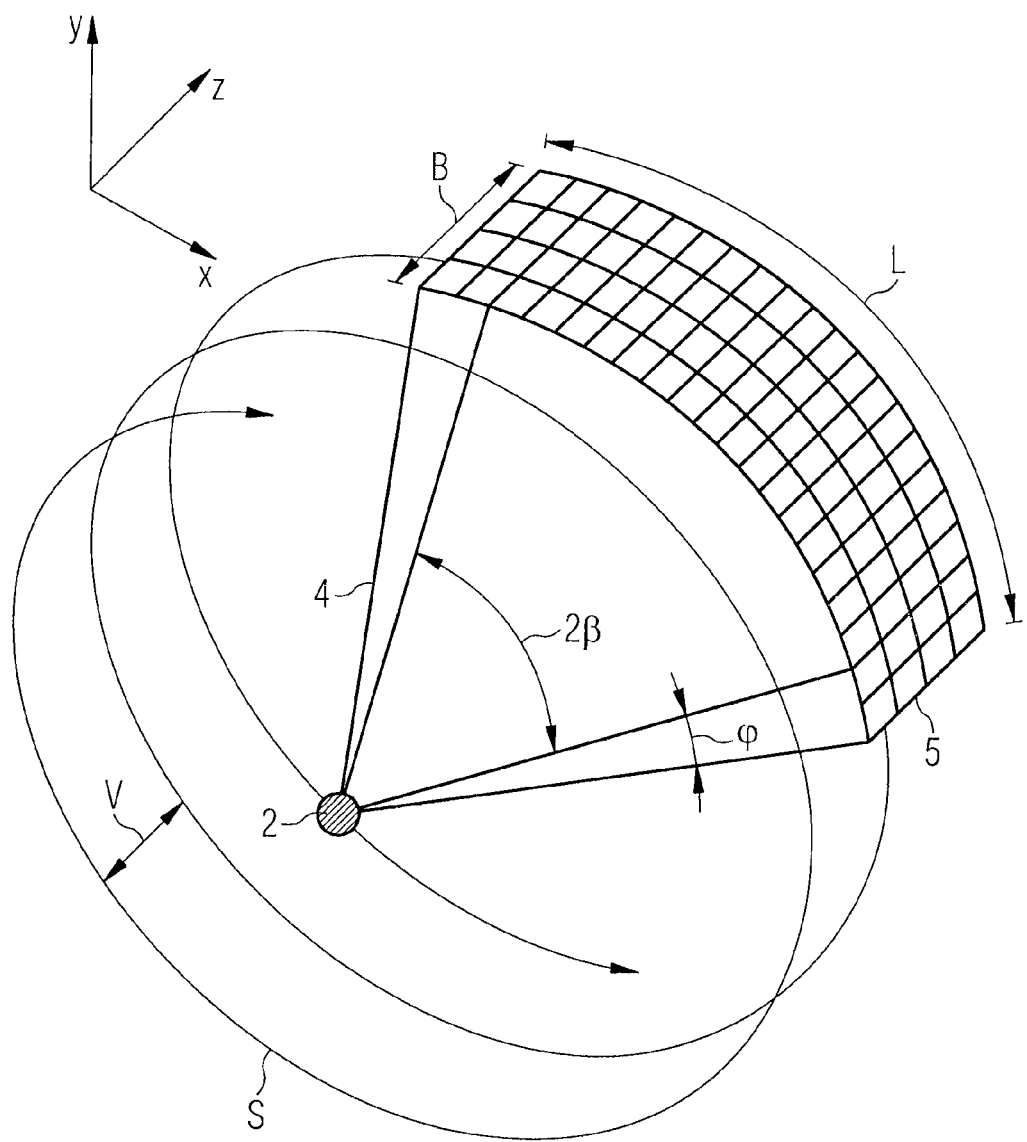
FIG. 3 shows a schematic representation of spiral-shaped focusing and detector movement.

FIGS. 1 and 2 show a spiral CT scanner that may be used for performing the method according to the present embodiments and has a multi-row detector. FIG. 1 schematically shows a gantry 1 having a focus 2 and a likewise rotating detector 5 (with width B and length L) in cross-section perpendicular to the z-axis. FIG. 2 shows a longitudinal section of the gantry 1 and the likewise rotating detector 5 in the direction of the z-axis. The gantry 1 has an X-ray beam source with the focus 2 and a collimator 3 close to the X-ray beam source and disposed in front of the focus 2. A bundle of rays 4, delimited using the collimator 3, runs from the focus 2 to the detector 5, which is oppositely disposed, penetrating the patient P situated between the focus 2 and the detector 5. The scanning takes place during the rotation of focus 2 and detector 5 around the z-axis, the patient P being moved simultaneously in the direction of the z-axis. As shown in FIG. 3, a helical path S (e.g., a scanning path) for focus 2 and detector 5 having a gradient or feed V is produced in the coordinate system of the patient P.

During the scanning of the patient P, dose-dependent signals acquired by the detector 5 are transmitted to a computing unit 7 via a data/control line 6. From the measured raw data, the spatial structure of a scanned region of the patient P is calculated in terms of absorption values in a known manner with the aid of known methods that are stored in program modules $P_1$ to $P_n$. In one embodiment, a theoretically exact reconstruction method is applied.

In other respects, the CT scanner is likewise operated and controlled using the computing unit 7 and a keyboard 9. The computing unit 7 may be a processor, computer, server or other device, configured with data stored in non-transitory computer readable media, for performing the acts described herein. Computed data may be output via a monitor 8 or a printer (not shown).

The majority of the efficiently usable approximate and exact reconstruction methods (e.g. those described in U.S. Pat. No. 6,771,733 B2) require the calculation of the derivative along the scanning path.

In the case of exact three-dimensional reconstruction methods, there are essentially three methods that are used for calculating the derivative along the scanning path: the "direct scheme"; the "chain rule scheme;" and the "new scheme" (cf. F. Noo, S. Hoppe, F. Dennerlein, G. Lauritsch, and J. Hornegger. "A New Scheme for View-Dependent Data Differentiation in Fan-Beam and Cone-Beam Computed Tomography." *Physics in Medicine and Biology* 52.17 (2007): 5393-5414.). The direct scheme is easy to implement and yields good results provided the scanning rate along the scanning path is high. It has been demonstrated, however, that if the scanning rate is too low the direct scheme fails to deliver usable results. The chain rule scheme generally copes better with a lower scanning rate. This does not apply unreservedly, however, since the chain rule scheme behaves like the direct scheme with certain types of scanning paths, such as, for example, a linear scanning path. Consequently, the chain rule scheme cannot be used without restriction when the scanning rate is too low. The new scheme was developed in order to solve this problem, so that usable results can still be achieved even with lower scanning rates. However, it is likely that a higher scanning rate will lead to more precise and consequently better results, even if a higher scanning rate is not essential for the use of the new scheme.

This is the starting point for the present embodiments. A departure is made from constant scanning in order to enable the number of scanning points to be reduced. Points on a trajectory are specified (e.g., equidistantly). A plurality of scanning points are specified for each of the specified points on the trajectory. The point of the trajectory for which the derivative is calculated does not necessarily coincide with one of the plurality of scanning points. This may be the case for an uneven number of scanning points per plurality of scanning points.

In contrast to the conventional scheme, in which only the interval between scanning points can be varied, it is possible in one embodiment to optimize the ratio of the number of scanning points to image quality by setting at least three variables such as, for example, a spacing of the points for which the derivative is calculated, a number of scanning points per derivative calculation and a spacing of the scanning points. FIG. 4 helps illustrate how this leads to a reduction in the total number of scanning points.

Curve A of FIG. 4 shows a conventional recording protocol using the example of a linear portion of an arbitrary scanning path. The points symbolize the scanning positions along the scanning path from which projections may be recorded. The distance between two adjacent scanning positions is constant along the scanning path. Curves B and C show two different variants of the recording protocol according to the present embodiments. The recording protocol from curve A serves as a basis in each case, as a result of which the number of recorded projections is initially increased by a factor 2 in curve B and by a factor 3 in curve C. Referring to the recording protocol in graph B, the side on which a new scanning position is not important, and the scanning positions in curve B may also be shifted relative to the scanning positions in curve A. Curves D and E show two different variants of the new recording protocol, a recording protocol having a scanning rate lower than the scanning rate in curve A, which again serves as a basis, by a factor of three. This enables the number of recorded projections in curve D to be reduced by 33% compared with curve A. In curve E, the number of recorded projections remains the same compared with curve A. In this case the number of recorded projections is dependent solely on the recording protocol used as a basis.

The invention is not limited to the cases described in the present embodiments. In particular, other recording protocols than are shown in FIG. 4 and other applications than spiral CT (e.g. CT imaging using a trajectory consisting of a circle and a line) may be used.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining attenuation coefficients for an object using a movable X-ray source and a detector, which is provided for recording projections, the method comprising:
    specifying a trajectory path for the movable X-ray source;
    specifying positions on the trajectory path for determining a derivative of projections recorded by the detector;
    specifying a plurality of scanning positions for each of the specified positions;
    following the trajectory path with the X-ray source and recording a projection for each scanning position of the pluralities of scanning positions;
    numerically calculating a projection derivative in relation to the trajectory path for each of the specified positions using the associated recorded projection for each scanning position of the pluralities of scanning positions; and
    determining attenuation coefficients for the object from the calculated projection derivatives using a theoretically exact or approximate rule for a reconstruction,
    wherein an interval between adjacent scanning positions that belong to the same plurality of scanning positions is smaller than an interval between adjacent scanning positions that belong to different pluralities of scanning positions.

2. The method as claimed in claim 1, wherein the X-ray source follows the trajectory path at a constant speed.

3. The method as claimed in claim 2, wherein the positions on the trajectory path for determining the derivative of projections recorded by the detector are specified equidistantly.

4. The method as claimed in claim 2, wherein the attenuation coefficients are determined in the course of a computed tomography scan.

5. The method as claimed in claim 1, wherein the positions on the trajectory path for determining the derivative of projections recorded by the detector are specified equidistantly.

6. The method as claimed in claim 5, wherein the attenuation coefficients are determined in the course of a computed tomography scan.

7. The method as claimed in claim 1, wherein the attenuation coefficients are determined in the course of a computed tomography scan.

8. A device for determining attenuation coefficients for an object using a movable X-ray source and a detector, which is provided for recording projections, the device comprising:
    a hardware computing unit configured to:
        specify a trajectory path for the movable X-ray source;
        specify positions on the trajectory path for determining a derivative of projections recorded by the detector;
        specify a plurality of scanning positions for each of the specified positions;
        numerically calculate a projection derivative in relation to the trajectory path for each of the positions using the projections recorded for the associated plurality of scanning positions; and
        determine attenuation coefficients for the object from the calculated projection derivatives using a theoretically exact or approximate rule for a reconstruction;
    the X-ray source operable to follow the specified trajectory path; and
    the detector operable to record a projection for each scanning position,
    wherein an interval between adjacent scanning positions that belong to the same plurality of scanning positions is smaller than an interval between adjacent scanning positions that belong to different pluralities of scanning positions.

9. The device as claimed in claim 8, wherein the device is part of a computed tomography system.

10. The device as claimed in claim 8, wherein the device is part of a computed tomography system.

11. In a non-transitory computer-readable storage medium that stores instructions executable by a computing unit to determine attenuation coefficients for an object using a movable X-ray source and a detector, which is provided for recording projections, the instructions comprising:
    specifying a trajectory path for the movable X-ray source;
    specifying positions on the trajectory path for determining a derivative of projections recorded by the detector;
    specifying a plurality of scanning positions for each of the specified positions;
    following the trajectory path with the X-ray source and recording a projection for each scanning position of the pluralities of scanning positions;
    numerically calculating a projection derivative in relation to the trajectory path for each of the specified positions using the associated recorded projection for each scanning position of the pluralities of scanning positions; and
    determining attenuation coefficients for the object from the calculated projection derivatives using a theoretically exact or approximate rule for a reconstruction,
    wherein an interval between adjacent scanning positions that belong to the same plurality of scanning positions is smaller than an interval between adjacent scanning positions that belong to different pluralities of scanning positions.

12. The non-transitory computer-readable storage medium as claimed in claim 11, wherein the X-ray source follows the trajectory path at a constant speed.

13. The non-transitory computer-readable storage medium as claimed in claim 11, wherein the positions on the trajectory path for determining the derivative of projections recorded by the detector are specified equidistantly.

* * * * *